(12) United States Patent
Borden

(10) Patent No.: US 7,773,211 B2
(45) Date of Patent: Aug. 10, 2010

(54) APPARATUS AND METHOD FOR DETERMINING STRESS IN SOLAR CELLS

(75) Inventor: Peter G. Borden, San Mateo, CA (US)

(73) Assignee: Applied Materials, Inc., Santa Clara, CA (US)

( * ) Notice: Subject to any disclaimer, the term of this patent is extended or adjusted under 35 U.S.C. 154(b) by 593 days.

(21) Appl. No.: 11/695,058

(22) Filed: Apr. 2, 2007

(65) Prior Publication Data
US 2008/0239315 A1  Oct. 2, 2008

(51) Int. Cl.
*G01N 21/00* (2006.01)
(52) U.S. Cl. .................. 356/237.4; 356/364; 356/237.5
(58) Field of Classification Search ......... 356/364–369, 356/237.2–237.5; 250/225
See application file for complete search history.

(56) References Cited

U.S. PATENT DOCUMENTS

| | | | |
|---|---|---|---|
| 5,828,500 A | 10/1998 | Kida et al. | |
| 6,608,689 B1 | 8/2003 | Wei et al. | |
| 6,825,487 B2 * | 11/2004 | Preece | 250/559.4 |
| 2004/0206891 A1 | 10/2004 | Ma et al. | |
| 2007/0019209 A1 | 1/2007 | Pfaff | |

* cited by examiner

*Primary Examiner*—L. G Lauchman
(74) *Attorney, Agent, or Firm*—Pillsbury Winthrop Shaw Pittman LLP

(57) ABSTRACT

A method and system as described herein provides for detecting certain anomalies in a wafer. According to one aspect, these anomalies relate to defects or stress that can lead to wafer breakage before, during or after further wafer processing. According to other aspects, the method includes passing polarized light through a wafer and analyzing the transmitted light for any changes in polarization. According to additional aspects, the method includes analyzing the entire wafer in one image capturing operation. According to still further aspects, the light passed through the wafer is below the bandgap for a material such as silicon that comprises the wafer, so that substantially all light will be transmitted through rather than absorbed or reflected by the material. According to still further aspects, the detection operation can be rapid and automatic, so that it can be easily included in an overall processing sequence. According to yet additional aspects, the detection includes analyzing different portions of the wafer differently, for example using different contrast ratios for edge and center portions of the wafer respectively.

23 Claims, 3 Drawing Sheets

APPARATUS AND METHOD FOR DETERMINING STRESS IN SOLAR CELLS

FIELD OF THE INVENTION

The present invention relates generally to characterizing materials during semiconductor device processing, and more particularly to a method and apparatus for identifying defects in semiconductor wafers, such as those wafers intended for use in solar cells, during device processing.

BACKGROUND OF THE INVENTION

Silicon solar cells are the most common type of photovoltaic conversion device today, comprising over 90% of the solar cell market. These devices are typically made using full wafers of silicon, and the silicon material is therefore a significant component of their cost. Given the cost, there is a motivation for decreasing the thicknesses of silicon wafers. For reference, a silicon wafer used in integrated circuit processing is 700-800 µm thick. Currently, solar cell wafers are on the order of 200 µm thick, and the trend is toward reducing this thickness in half.

A typical solar cell factory processes high quantities of such wafers. A square wafer 205 mm on a side produces approximately 6.7 watts of electricity, assuming 0.1 w/cm$^2$ incident power and 16% efficiency. Approximately 150,000 wafers must be processed to make 1 megawatt of solar cells. A typical factory produces 50 megawatts, equal to about 850 wafers per hour.

While the trend continues to make wafers thinner, one problem that makes it difficult to achieve and maintain such high processing throughput is the potential for wafer breakage. If a wafer breaks during processing, in many cases an operator must intervene to clean out the debris. Such events, if frequent, can seriously affect the line throughput and increase the cost of processing.

Some previous attempts at detecting defects in semiconductor wafers have been made. For example, U.S. Patent Pub. No. 2004/0206891 to Ma et al. describes a non-destructive process for detecting defects in a semiconductor wafer such as micropipes and screw dislocations by illuminating the wafer with polarized light. However, Ma et al. do not detail the possible light sources that are used, and the ability to transmit visible light through wafers comprised of materials other than the SiC material described by Ma et al. may be limited. So a reliable way of detecting defects in wafers comprised of other types of materials is not possible based on Ma et al.'s teachings. Moreover, Ma et al. are limited to analyzing sub-regions of a wafer and do not allow for rapid scanning of an entire wafer at a time. Still further, polarized light from Ma et al.'s system may enter a wafer at oblique angles, especially in compact systems, which can further degrade the performance of the polarization measurement.

Therefore, there remains a need for methods to detect defects in starting wafers that can lead to breakages, and particularly methods that can be implemented before or together with other in-line processes.

SUMMARY OF THE INVENTION

The present invention provides a method and system for detecting certain anomalies in a wafer. According to one aspect, these anomalies relate to defects or stress that can lead to wafer breakage before, during or after further wafer processing. According to other aspects, a method according to the invention includes passing polarized light through a wafer and analyzing the transmitted light for any changes in polarization. According to additional aspects, a method includes analyzing the entire wafer in one image capturing operation. According to still further aspects, the light passed through the wafer is below the bandgap for a material such as silicon that comprises the wafer, so that substantially all light will be transmitted through rather than absorbed or reflected by the material. According to other aspects, the light source is accurately collimated so that polarization is defined in the plane of the wafer. According to still further aspects, the detection operation can be rapid and automatic, so that it can be easily included in an overall processing sequence. According to yet additional aspects, the detection includes analyzing different portions of the wafer differently, for example using different contrast ratios for edge and center portions of the wafer respectively.

In furtherance of these and other objects, an example method for analyzing a wafer according to the invention includes determining an appropriate light source for the wafer, illuminating the wafer with polarized light from the determined light source, filtering light transmitted through the wafer in accordance with a polarization orientation of the polarized light, and analyzing the filtered light to identify anomalies in the wafer. In additional furtherance of the above and other objects, another example method for analyzing a silicon wafer according to the invention includes preparing a light source having a wavelength that is capable of substantially transmitting through the silicon wafer, illuminating all portions of the silicon wafer with light from the light source, filtering light transmitted through the silicon wafer in accordance with a polarization orientation of the polarized light, capturing an image of the filtered light with a camera, and analyzing the captured image to identify anomalies in the silicon wafer.

BRIEF DESCRIPTION OF THE DRAWINGS

These and other aspects and features of the present invention will become apparent to those ordinarily skilled in the art upon review of the following description of specific embodiments of the invention in conjunction with the accompanying figures, wherein.

DETAILED DESCRIPTION OF THE PREFERRED EMBODIMENTS

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements. Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

A general principle according to aspects of the invention is to pass polarized light through a wafer and to analyze the transmitted light for any changes in polarization. A normal, unstressed wafer will transmit light uniformly. However, stress in the wafer will induce birefringence, which will result in local rotation of the polarization direction. These non-uniformities can thereby be imaged and further analyzed to determine possible risks of wafer failure. Another general principle of the invention is to determine the wavelength of a light source that is suitable to use, the suitability being determined, for example, based on the material and other properties of the wafer to be analyzed. Yet another principle according to the invention is to provide an accurately collimated light source so that polarization is defined in the plane of the wafer to be analyzed. It should be apparent that not all of these principles need be practiced in combination.

Figure 1:
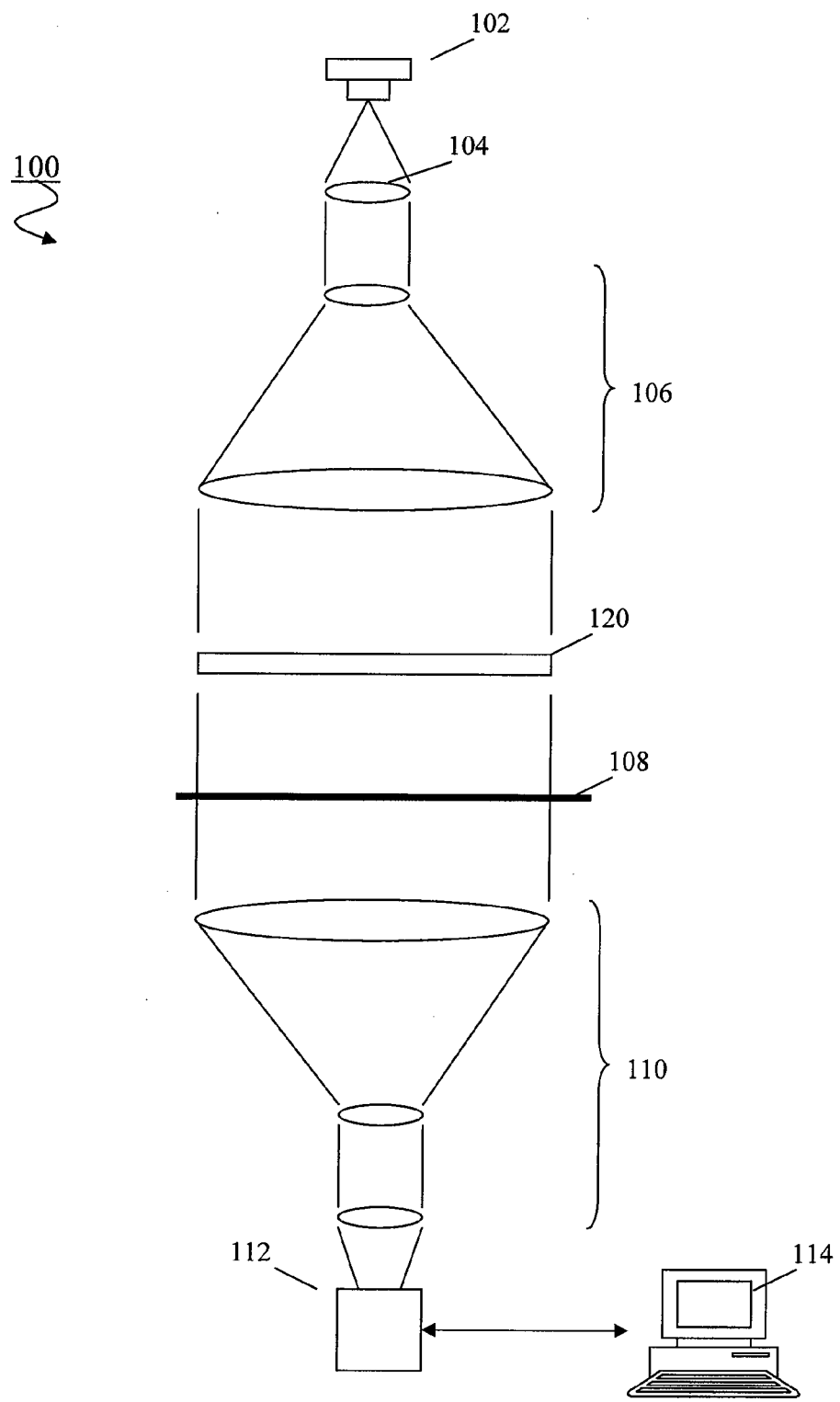
FIG. 1 is a block diagram illustrating one example implementation of the invention.

FIG. 1 is a diagram illustrating one possible embodiment of the invention. As shown in FIG. 1, a system 100 for identifying potential stress in a wafer 120 includes a light source 102 that illuminates a collimating lens 104. Collimated light from lens 104 is expanded by beam expander 106 and passes through wafer 120. Light passing through wafer 120 is polarized by polarizer 108. The polarized light is focused by imaging optics 110 and captured by camera 112. The captured image can then be processed by processor 114.

It should be noted that the configuration of FIG. 1 is illustrative rather than limiting, and that there are many equivalent configurations of the same, additional or fewer optical components that can obtain similar optical results. For example, mirrors and additional lenses may be used depending on circumstances. Moreover, the ordering of components in the end-to-end optical path may be changed. For example, polarizer 108 may be placed between lenses in imaging optics 110 so that it can be smaller than if placed as shown in FIG. 1.

In one example implementation of this embodiment, where wafer 120 is a silicon wafer having a thickness of about 200 μm, light source 102 is comprised by a 980 nm laser diode. Although this wavelength lies above the silicon bandwidth, the absorption length of silicon at this wavelength is on the order of 150 μm, so a sufficient amount of light transmits through a silicon wafer having a thickness of about 200 μm. Advantages of using a light source 102 having this wavelength include the ready availability of low cost, high reliability laser diodes and the ability to use a low cost silicon CCD camera as camera 112 to image the transmitted light. Moreover, using a laser diode as a light source is preferred because it emits polarized light. Still further, many 980 nm lasers are available with optical fiber outputs. This circularizes the beam, making it easier to work with in subsequent optical components in the optical path. It should be noted that the invention is not limited to wafers comprised of silicon, and the principles of the invention can be extended to other types of unprocessed or processed wafers such as SiC, GaAs, Ge, or thin film solar cells.

As shown in FIG. 1, the laser beam is first collimated and then expanded to a size greater than the wafer 120. In one typical example, wafer 120 is a silicon wafer having a thickness of about 200 μm and may have a circular, square or pseudo-square (square with rounded corners) shape. Typical square wafers are 125, 156 or 210 mm on a side. In this example where light source 102 is a laser diode, collimating lens 104 is a commercially available laser diode collimating lens such as part 06GLC002 from Melles Griot of Carlsbad, Calif., and beam expander is comprised of two lenses positioned about 5 cm from lens 104 and about 10 cm from wafer 120. As shown in FIG. 1, preferably the final lens in the arrangement has a diameter at least as great as the diagonal measure of a wafer to be analyzed. This enables the system 100 to image the entire wafer in one view. Moreover, this arrangement ensures that the polarization of the collimated light incident on the wafer will be substantially defined (i.e. within about ±10%) in the plane of the wafer over the full field of view. While this example implementation is preferred, lesser expansion may also be used, resulting in smaller fields of view.

Returning to FIG. 1, the transmitted light from wafer 120 passes through a polarizer 108 such as a high contrast polarizer (e.g. part number 03FPC017 from Melles Griot of Carlsbad, Calif. in an example configuration where polarizer 108 is between lenses in optics 110) oriented at approximately 90 degrees to the plane of polarization of the source. As will be appreciated by those skilled in the art, this nulls the beam having the same polarization as the source—thereby providing minimum transmission of a beam in the absence of a wafer. Therefore, any regions of stress that result in a polarization rotation appear as bright spots on a dark background. This configuration also minimizes saturation of the camera.

Following or in conjunction with polarization, imaging optics 110 focuses the transmitted light onto the imaging plane of the camera. In a preferred example, the optical system is symmetric with respect to wafer 120, and so imaging optics 110 comprise a pair lenses positioned similarly with respect to wafer 120 as expander 106 and that compress the light in an amount corresponding to the amount it is expanded by lenses 106. The compressed beam may be shone directly into the camera 112, or further compressed using the final lens in the pair 110. In this example, camera 112 is comprised of a conventional CCD camera with a 0.5 in. imaging element. Finally, the camera output feeds into a processor 114 that automatically analyzes the image for regions of stress.

In embodiments, processor 114 is comprised of a computer such as a Windows PC running image processing software that is adapted to automatically receive and process images captured by camera 112. In one example the software compares the captured image to a normalized image and uses different contrast ratios in different regions of the wafer to detect anomalies associated with bright spots having a predetermined threshold. For example, the software can use a higher contrast ratio near edge regions, where bright spots would indicate cracks or similar defects. Meanwhile regions nearer the center of the wafer would tend to be more uniform, so a lower contrast ratio can be used and bright spots above a similar or lower predetermined threshold than in the edge regions would indicate built-in stress. Those skilled in the art will be able to implement software for processor 114 using known or other image processing programs based on the examples and teachings provided herein.

In this example where software automatically detects defects in a wafer, the processor 114 may further cause a visible or audible alarm to sound, or may be coupled to control other equipment that identifies the wafer as defective and/or removes the wafer from further processing. Alternatively or additionally, processor 114 may include a monitor that allows an operator to view the image captured by camera 112, perhaps along with other text or graphical indicia inserted by software to identify potential defects in a wafer corresponding to the captured image. Those skilled in the art will understand how to implement additional functionality for these various embodiments, and so details thereof will be omitted here for sake of clarity of the invention.

In one preferred application of the invention, system 100 is provided in a stage of a wafer process such that each wafer 120 passes through system 100 before wafer processing begins. This provides a rapid way to inspect incoming all wafers for stress, and to preemptively screen out wafers that are at the risk of breaking. It should be noted that many types of stress can be detected such as edge cracks, chips, roughness or strain, and line or point defects within the wafer. Moreover, the system can simultaneously image edge defects such as nicks that could be starting points for the wafer to cleave. Defective wafers can be rejected at this point, before they enter the automation system where they are at risk of breaking.

Figure 2:
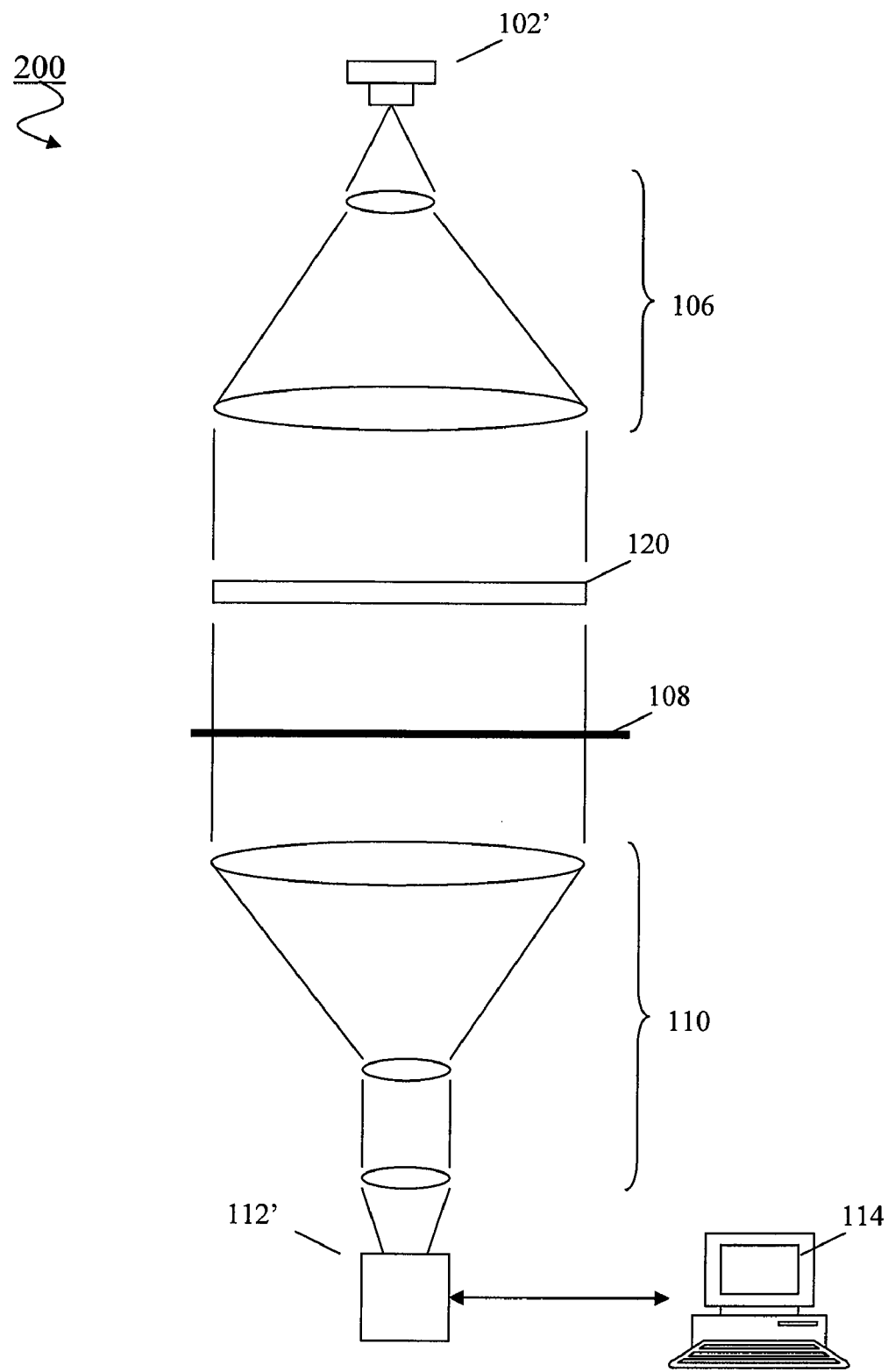
FIG. 2 is a block diagram illustrating another example implementation of the invention.

Another preferred embodiment of the invention is shown in FIG. 2. In this example, differently from the previous embodiment, light source 102' is comprised of a sub-bandgap laser, such as a laser having a wavelength of 1.3 or 1.5 µm. Silicon readily transmits light at these infrared wavelengths. Laser sources are preferred, as these provide a polarized output, and so this embodiment does not need a collimator 104 as in the previous embodiment. However, other sources such as lamps with filters and polarizers may also be used.

Those skilled in the art will be able to understand how to implement this embodiment with similar components shown in FIG. 2 as in the previous example after being taught by the previous example. However, it should be noted that another difference in this embodiment is the use of an alternate camera 112', which is for example an IR imaging camera. In this example, camera 112' is implemented by an infrared viewer that converts infrared images to visible light such as those available from Newport Corporation, followed by a CCD such as that described in the previous embodiment. Alternatively, camera 112' may be implemented by a focal plane array.

Figure 3:
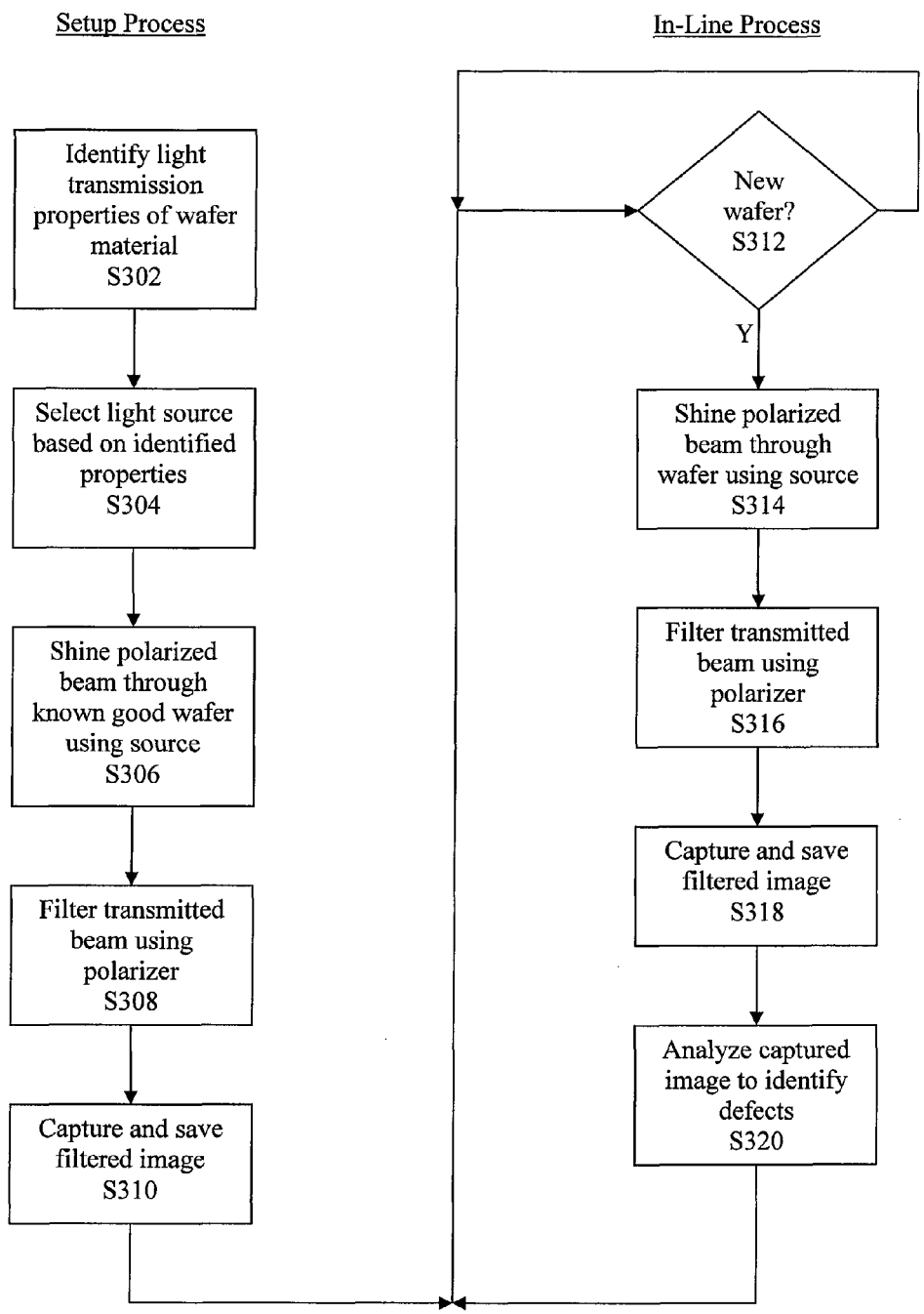
FIG. 3 is a flowchart illustrating an example method for detecting wafer defects according to aspects of the invention.

FIG. 3 is a flowchart illustrating an example method of detecting wafer defects according to the invention.

As shown in FIG. 3, an example method includes a setup process that can be implemented before an in-line process for detecting wafer defects. In this example, a setup process includes identifying light transmission properties of a wafer material (S302). Accordingly, this step includes identifying the wafer material, and its light transmission properties such as bandgap and absorption length. These identified properties are used in a next step (S304) to determine an appropriate light source. As shown above, this can include using an infrared light source for certain wafer materials such as silicon, because such a light source is below the bandgap of silicon. As similarly shown above, since the absorption length of silicon is about 150 µm for a 980 nm light source, such a light source may be appropriate if a silicon wafer has a thickness of 200 µm or less. Those skilled in the art will be able to implement these steps with various wafer materials, thicknesses and light sources based on these non-limiting examples.

In step S306, a polarized beam using the selected light source is shown through a known good wafer, for example using the configuration shown in FIG. 1 or 2. In a preferred example, the beam is expanded so that the entire wafer is illuminated. However, the invention can be practiced by illuminating different regions of the wafer, and repeating certain of the described process steps accordingly. The transmitted beam through the wafer is then polarized in step S308, for example using a polarizer oriented 90 degrees from the polarization orientation of the beam. The filtered beam is then captured and saved as a "normalized" image for subsequent processing in step S310.

Steps S312 to S320 illustrate one embodiment of how the invention can be implemented in an overall wafer process. In this example, when a new wafer is ready to be analyzed (determined in step S312), a polarized light beam is shone through it from the same light source and using the same configuration as used in the setup process (step S314). Similarly, the transmitted beam is filtered through a polarization filter as described above (step S316), and the filtered image is captured and saved (step S318). The captured image can then be compared against the normalized image to identify defects using, for example, image processing software as described above (step S320). Appropriate action can then be taken for wafers identified as defective, for example by removing them from the line so that they are not introduced to subsequent processing.

FIG. 3 shows an example embodiment including a setup process (steps S302-S310) and an in-line process (steps S312-S320). However, it should be apparent that these processes need not be implemented together or at the same time. Moreover, certain steps (e.g. steps S306-S312 for capturing a "normalized" image) can be implemented in either or both processes.

Although the present invention has been particularly described with reference to the preferred embodiments thereof, it should be readily apparent to those of ordinary skill in the art that changes and modifications in the form and details may be made without departing from the spirit and scope of the invention. It is intended that the appended claims encompass such changes and modifications.

What is claimed is:

1. A method for analyzing a wafer comprising:
   determining an appropriate light source for the wafer;
   illuminating the wafer with polarized light from the determined light source;
   filtering light transmitted through the wafer in accordance with a polarization orientation of the polarized light; and
   analyzing the filtered light to identify anomalies in the wafer,
   wherein the step of determining the appropriate light source includes identifying light transmission properties of the wafer.

2. A method according to claim 1, wherein the wafer is comprised of silicon.

3. A method according to claim 1, wherein the polarized light is linearly polarized.

4. A method according to claim 3, wherein the filtering includes using a linear polarizer.

5. A method according to claim 4, wherein the polarizer is oriented at approximately 90 degrees to the polarization orientation of the light source, thereby forming a null in the filtered light except for portions associated with the anomalies.

6. A method according to claim 1, further comprising capturing an image of the filtered light, wherein the analyzing step includes analyzing the captured image.

7. A method according to claim 1, wherein the light transmission properties include a bandgap of a material comprising the wafer.

8. A method according to claim 1, wherein the light transmission properties include an absorption length of a material comprising the wafer.

9. A method for analyzing a wafer comprising:
   determining an appropriate light source for the wafer;

illuminating the wafer with polarized light from the determined light source;

filtering light transmitted through the wafer in accordance with a polarization orientation of the polarized light; and analyzing the filtered light to identify anomalies in the wafer, wherein the step of determining the appropriate light source includes determining a wavelength of the light source that will substantially transmit through the wafer.

10. A method according to claim 1, wherein the light source transmits polarized light.

11. A method according to claim 1, wherein the illuminating step includes transmitting unpolarized light from the light source and polarizing the unpolarized light.

12. A method according to claim 1, wherein the illuminating step includes illuminating all portions of the wafer at one time.

13. A method according to claim 1, wherein the light source comprises a laser diode.

14. A method for analyzing a wafer comprising:

determining an appropriate light source for the wafer;

illuminating the wafer with polarized light from the determined light source;

filtering light transmitted through the wafer in accordance with a polarization orientation of the polarized light; and analyzing the filtered light to identify anomalies in the wafer, wherein the analyzing step includes comparing the filtered light to an image of captured light transmitted through a known good wafer using the light source.

15. A method for analyzing a wafer comprising:

determining an appropriate light source for the wafer;

illuminating the wafer with polarized light from the determined light source;

filtering light transmitted through the wafer in accordance with a polarization orientation of the polarized light; and analyzing the filtered light to identify anomalies in the wafer, wherein the analyzing step includes separately analyzing filtered light through edge regions of the wafer using a first analysis, and analyzing filtered light through center portions of the wafer using a second different analysis.

16. A method according to claim 15, wherein the first and second analyses include using different contrast ratios.

17. A method according to claim 1, wherein the illuminating step includes collimating the polarized light.

18. A method according to claim 17, wherein the collimating step is performed such that polarization is substantially defined in the plane of the wafer.

19. A method for analyzing a silicon wafer comprising:

preparing a light source having a wavelength that is capable of substantially transmitting through the silicon wafer;

illuminating all portions of the silicon wafer with polarized light from the light source;

filtering light transmitted through the silicon wafer in accordance with a polarization orientation of the polarized light;

capturing an image of the filtered light with a camera, wherein only a single iteration of the illuminating, filtering and capturing steps is needed to ensure that the all portions of the silicon wafer are included in the captured image; and analyzing the captured image to identify anomalies in the silicon wafer.

20. A method according to claim 19, wherein the light source is a 980 nm laser diode.

21. A method according to claim 19, wherein the light source is an infrared laser.

22. A method according to claim 19, wherein the illuminating step includes collimating the polarized light.

23. A method according to claim 22, wherein the collimating step is performed such that polarization is substantially defined in the plane of the wafer.

* * * * *